(12) United States Patent
Jones

(10) Patent No.: US 7,365,838 B2
(45) Date of Patent: Apr. 29, 2008

(54) SYSTEM AND METHOD FOR THE MEASUREMENT OF OPTICAL DISTORTIONS

(75) Inventor: Michael I. Jones, Azle, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 52 days.

(21) Appl. No.: 10/817,538

(22) Filed: Apr. 2, 2004

(65) Prior Publication Data

US 2005/0219522 A1   Oct. 6, 2005

(51) Int. Cl.
*G01N 21/00* (2006.01)

(52) U.S. Cl. .................................. 356/239.1; 356/124

(58) Field of Classification Search .. 356/239.1–239.8, 356/237.1–237.5, 430–431
See application file for complete search history.

(56) References Cited

U.S. PATENT DOCUMENTS

| | | | | |
|---|---|---|---|---|
| 3,723,010 A | * | 3/1973 | McCrickered et al. | 356/124 |
| 3,912,395 A | * | 10/1975 | Voggenthaler | 356/124 |
| 4,299,482 A | * | 11/1981 | Task | 356/124 |
| 4,310,242 A | * | 1/1982 | Genco et al. | 356/128 |
| 4,461,570 A | * | 7/1984 | Task et al. | 356/239.1 |
| 4,647,197 A | * | 3/1987 | Kitaya et al. | 356/239.1 |
| H000999 H | * | 12/1991 | Merkel et al. | 356/239.1 |
| 5,343,288 A | * | 8/1994 | Cohen et al. | 356/239.1 |
| 5,471,297 A | * | 11/1995 | Tani | 356/239.1 |
| 5,621,520 A | * | 4/1997 | Hoffman | 356/124.5 |
| 5,812,260 A | * | 9/1998 | Louisnathan | 356/239.1 |
| 6,208,412 B1 | * | 3/2001 | Ladewski | 356/239.1 |
| 7,038,791 B2 | * | 5/2006 | Smith | 356/520 |

\* cited by examiner

*Primary Examiner*—Hoa Q. Pham
(74) *Attorney, Agent, or Firm*—Bracewell & Giuliani LLP

(57) ABSTRACT

An apparatus measures optical deviations caused by an aircraft canopy. In this apparatus, a light source generates a beam of light. A collimator, optically coupled to the light source, then collimates the beam of light. An optical assembly patterns the collimated beam of light into a patterned array of subaperture beams, which is directed onto an imaging screen. The patterned collimated beam of light produces images, which are electronically imaged and recorded to memory. An undistorted image results when the aircraft canopy is not placed in a path of the patterned collimated beam of light. However, a distorted image results when the aircraft canopy is placed in a path of the patterned collimated beam of light and distorts the patterned collimated beam of light. A processing unit compares the distorted image to the undistorted image to determine the optical distortions caused by the aircraft canopy.

25 Claims, 15 Drawing Sheets

SYSTEM AND METHOD FOR THE MEASUREMENT OF OPTICAL DISTORTIONS

GOVERNMENT INTEREST

This invention was made with Government support under Contract Number F33657-91-C-0006 awarded by The Department of the Air Force. The Government has certain rights in this invention.

TECHNICAL FIELD OF THE INVENTION

The present invention relates generally to the measurement of optical distortions, and more particularly, a system and method to rapidly measure the optical distortions of an aircraft canopy.

BACKGROUND OF THE INVENTION

Aircraft canopies protect the pilot from direct exposure to the flight environment while ideally providing the largest possible unobstructed view from the cockpit. In new fighter aircraft, the exterior shapes of the canopy typically include compound curvatures. These compound shapes are imposed by aerodynamic, structural, bird strike safety and electromagnetic signature requirements. In order to satisfy structural and bird strike safety requirements, plastic-based canopies have become quite thick to withstand these stresses. These thick canopies introduce strong refractive optical power and distortion into the view of the outside world. These optical distortions vary with target azimuth, elevation, and the pilot's eye (x, y, z) position. The distortions thus also vary between the left and right eye at any given viewing direction.

Canopy optical distortions interfere with the accuracy of visual cueing, and must be measured and compensated for in positioning of heads-up display (HUD) or helmet mounted display (HMD) symbology. Canopy manufacturing processes introduce additional optical distortions having even higher spatial frequencies than the basic canopy refractive properties. Unfortunately, these additional manufacturing distortions are unique to each canopy, with no two canopies ever exhibiting identical optical distortions. This situation is made worse as even more complex canopies are planned for new aircraft. These canopies are anticipated to have unique optical distortion characteristics. These unique optical characteristics necessitate the design, manufacture and use of mapping fixtures to individually measure canopy optical distortions over the specified field of regard (FOR) and region around design eye for each canopy produced. These variable optical distortions further necessitate algorithms that dynamically position HUD or HMD symbology based on each canopy's set of optical unique distortions and the pilot's moving head position within the 3-D pilot eye volume (PEV).

Previous mapper solutions sequentially project collimated light from a single small target at a series of scripted azimuth and elevation angles through the test canopy and into a camera lens. The camera is located at or near the pilot's design eye location. The camera forms an image of the projected target. Post-processing software calculates the (x, y) position of the target image and the corresponding azimuth/elevation angular deviation. This method gives very good accuracy and repeatability, on the order of 0.1-0.2 milliradians or better, at each particular measurement angle and eye position.

The principle disadvantage of this method is that only a single angular deviation value is measured at a time. The canopy is positioned on the fixture to place the imaging camera at one specific eye position, and the optical deviations of a scripted array of azimuth and elevation angles are sequentially measured at that eye point. The canopy must then be re-positioned on the fixture to the next eye position, and the same script of azimuth and elevation angle measurements repeated. Typically a minimum of five eye positions are measured, one at design eye, one above, one below, and two more at left and right of design eye. Newer fighter aircraft employing wide field-of-regard HMD's require many more eye positions over the 3-D PEV to be measured as well. The final reported optical deviation and symbology position compensation at any given azimuth and elevation is but a single, fixed weighted least squares composite average of the overlapping deviations from the different eye positions. Symbology positions projected on HUD's or HMD's cannot change with head (x, y, z) position, even though canopy optical distortions are continuously changing with eye position. Thus, projected symbology does not overlay exterior imagery over the complete viewing solid angle and PEV to the accuracies required by the new weapons systems.

Furthermore, sequential measurements can take an hour or more just for the relatively small angular solid angle of measurements needed for the HUD, and 8-10 hours or more for larger solid angles such as required for F-16 HMD's. These long measurement times dictate relatively sparse optical deviation data sampling. Sparse sampling reduces the accuracy of post-measurement curve fitting and symbology placement. New systems such as those employed by the F-35 aircraft require that deviation measurements be taken over a very large field of regard (FOR) for a tactical fighter aircraft, and over a very large 3-D PEV. The need for large solid angle coverage and larger 3-D PEV, combined with increased accuracy requirements on symbology placement, essentially renders previous sequential, discrete measurement methods totally impractical. No previous or present optical deviation mapping fixtures have the means to resolve this deficiency.

Therefore a need exists for a means to rapidly measure optical deviations created by an aircraft canopy through many possible 3-D locations of a pilot's eye within the canopy. Additionally, a need exists for a system and method capable of taking measured optical deviations and dynamically applying corrections to these deviations to dynamically align symbology within an HMD field of view to exterior images.

SUMMARY OF THE INVENTION

The present invention relates generally to the measurement of optical distortions. More particularly, the present invention provides a system and method to rapidly measure the optical distortions of an aircraft canopy that substantially addresses these needs as well as others.

One embodiment provides a method with which to determine optical deviations caused by an aircraft canopy. This involves generating a collimated beam of light of sufficient aperture to fully illuminate the 3-D PEV with some margin. The collimated beam of light then passes through an optical mask (termed a Hartmann mask) to produce an array pattern of sub-apertures, each projecting separate smaller collimated beams of light. The pattern of sub-aperture collimated beams of light is directed onto an imaging screen to produce multiple sub-aperture images, wherein the images are digitally imaged and are then stored in memory. When the canopy is not in the path of the patterned collimated beams of light, an undistorted image results and is stored in memory. When the canopy is in the path of the patterned collimated beams of light, a distorted image results as the aircraft canopy distorts the individual patterned collimated beams of light. The distorted image and is stored in memory. The distorted image is compared to the undistorted image to determine the optical distortions caused by the aircraft canopy.

The collimated beam of light is generated external to the aircraft canopy, masked with the Hartmann sub-aperture mask, and imaging screens and cameras located within the aircraft canopy in a first embodiment. A second embodiment generates the Hartmann sub-aperture collimated beams of light within the aircraft canopy and the imaging screens and cameras are located outside the aircraft canopy. Both embodiments allow the collimated beams of light to be directed to or from the pilot's eye centroid over the full 3-D PEV from varying combinations of elevation and azimuth angles.

Another embodiment provides an apparatus to measure optical deviations caused by an aircraft canopy. In this apparatus, a light source generates a beam of light. A collimator lens or mirror, optically coupled to the light source, then collimates the beam of light. A Hartmann mask patterns the collimated beam of light into smaller sub-apertures of collimated light, which are directed onto an imaging screen. The patterned collimated beams of light produce images, which are recorded to computer memory with analog or digital imaging cameras. An undistorted image results when the aircraft canopy is not placed in a path of the patterned collimated beam of light. However, a distorted image results when the aircraft canopy is placed in a path of the patterned collimated beams of light and distorts the patterned collimated beam of light. A processing unit compares the distorted image to the undistorted image to determine the optical distortions caused by the aircraft canopy. One embodiment locates the light source, collimator, and Hartmann mask outside the aircraft canopy and the imaging screen within the aircraft canopy. Another embodiment reverses this relationship.

Yet another embodiment provides an apparatus to determine optical deviations caused by an aircraft canopy. This embodiment places a contrasting optical pattern external to the aircraft canopy. A camera located within the pilot's eye centroid captures both an undistorted image when the aircraft canopy is not placed between the camera and the contrasting optical pattern, and a distorted image when the aircraft canopy is placed between the camera and the contrasting optical pattern. A processing unit receives and stores the undistorted image and distorted image in memory operably coupled to the processing unit. The processing unit also compares the distorted image to the undistorted image to determine the optical distortions caused by the aircraft canopy.

The wavefront-error determination provided by the present invention greatly improves the measurement accuracy and speed of canopy optical deviation data. Further, proven wavefront error reconstruction algorithms and associated software can accurately reconstruct canopy angular deviations at any azimuth and elevation for any continuously varying point within the PEV. This enables greatly improved visual cueing and alignment between computer-generated symbology and real world images external to the aircraft that also dynamically accounts for the optical distortions of the aircraft canopy.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein:

FIGS. 4A-4E provide Hartmann spot patterns for a cylindrical canopy where the distance from focus is varied;

DETAILED DESCRIPTION OF THE INVENTION

Figure 1A:
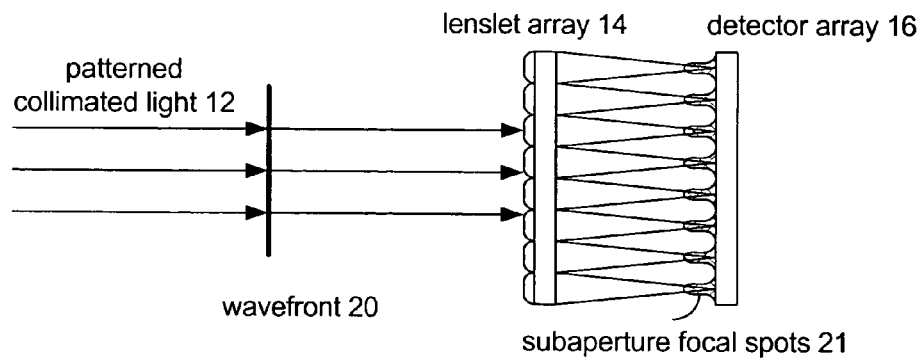
FIGS. 1A and 1B depict an incoming optical wave front and the optical effect a canopy has on this wave front.

Preferred embodiments of the present invention are illustrated in the FIGUREs, like numerals being used to refer to like and corresponding parts of the various drawings.

The present invention provides a means for measuring canopy optical deviations accurately and over a large field of regard (FOR) and large PEV. Additionally, the present invention allows these measurements to be made in a rapid and massively parallel manner when compared to previous methods, as the wavefront errors over the entire PEV are measured and calculated with a single pair of camera images. These improvements in measurement speed and accuracy are coupled with algorithms that dynamically compensate for canopy optical distortion and HMD symbology placement as a function of head position. This results in improved visual cueing and alignment between computer generated symbology and exterior images.

One embodiment provides a novel concept for canopy characterization and measurement. This concept directly measures transmitted wavefront error. An optical wavefront is defined as a continuous surface of constant optical phase at any instant in time. Light emitted, reflected or scattered from distant objects illuminates the entire aircraft, canopy, cockpit, pilot and immediate region around design eye with optical wavefronts. The portion of incident light transmitted through the canopy into the cockpit illuminates the pilot with an optical wavefront distorted by the canopy's optical and refractive properties and manufacturing errors. The transmitted canopy wavefront error profile continuously varies with illumination azimuth and elevation angle, and fully illuminates the pilot's helmet, visor and face at each angle. Optical rays are 2-D gradients (surface normals) perpendicular to this transmitted wavefront profile at any given point on the wavefront profile. A distorted wavefront produces corresponding angular deviations of its surface normals. These angular deviations are viewed as optical distortion of the outside world and vary with wavefront (x, y, z). Thus, a pilot may experience different optical deviations between the left and right eyes. These optical deviations further vary as the pilot's head is repositioned.

The 3-D portion of the canopy transmitted wavefront error of interest for accuracy and HMD symbology placement may be referred to in this disclosure as the Pilot Eye Volume (PEV). The total 3-D excursion range of pilot neck, head and eye motion sets the dimensions of the PEV, as well as the seat height setting and any additional imaging camera locations. The pilot's eye pupils or helmet camera pupils dynamically sample a very small portion of this total transmitted wavefront error.

Existing wavefront error sensors have been developed to support high-energy atmospheric laser applications. Free-stream atmospheric turbulence produces highly inhomogeneous air density distributions and corresponding optical wavefront errors due to changing local index of refraction along the laser beam's path. These density fluctuations vary rapidly in spatial distribution, frequency and strength, having bandwidths on the order of several hundred hertz. Compounded with these free stream propagation wavefront errors are those introduced by the local aerodynamic flow-fields surrounding the beam director telescope. These flow-field wavefront errors have even higher bandwidths, ranging up to several kilohertz. Wavefront error sensing devices exist that can measure dynamic wavefront errors at speeds exceeding 10 KHz with as many as 128×128 discrete subaperture samples.

The aircraft canopy transmitted wavefront error is a function of azimuth and elevation angle. Thus, the bandwidth of canopy wavefront error measurement is proportional to the speed the mapping fixture scans the required field of regard. Very high-speed wavefront sensors allow canopy wavefront errors to be measured at very high sampling rates. This is in great contrast to current slower step/stare image acquisition as is done in current mappers. The entire wavefront error at each azimuth and elevation angle over the entire pilot eye volume (PEV) is measured as a single image. This eliminates the need to repeat the azimuth/elevation script for different eye positions.

In one embodiment, light from a collimator is aimed through the canopy and at the center of the PEV at a scripted azimuth and elevation angle. This collimator may be located inside or external to the canopy. The collimated light passes through a mask to produce multiple subapertures. Each subaperture then emits collimated light that passes through the canopy at the PEV. Imaging optics collect the patterned collimated light to create an image. The imaging optics are positioned external or internal to the canopy, where the collimator is located on the opposite side of the canopy. The imaging optics have sufficient aperture to intercept the deviated rays of collimated light from each subaperture.

The resulting imagery is processed with a processing unit. The processing unit may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The memory 34 may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processing unit implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory stores, and the processing unit executes, operational instructions corresponding to at least some of the steps and/or functions illustrated in FIGS. 12, 13, and 14.

The resulting imagery is processed using data reduction and error reconstruction algorithms embedded within software. These result in a highly sampled and very accurate representation and reconstruction of the wavefront error at the scripted azimuth and elevation.

One application senses the location of the pilot's head within the canopy and supplies this information to wavefront reconstructor software that dynamically calculates the wavefront error at that azimuth and elevation, at any continuous point or pair of points in the 3-D PEV.

Dynamic reconstruction of the canopy wavefront error as a function of head position enables dynamic positioning of the symbology on the HMD. This greatly improves visual cueing and designation accuracy. Furthermore, this allows the HMD system to provide improved accuracy and performance.

Figure 1B:
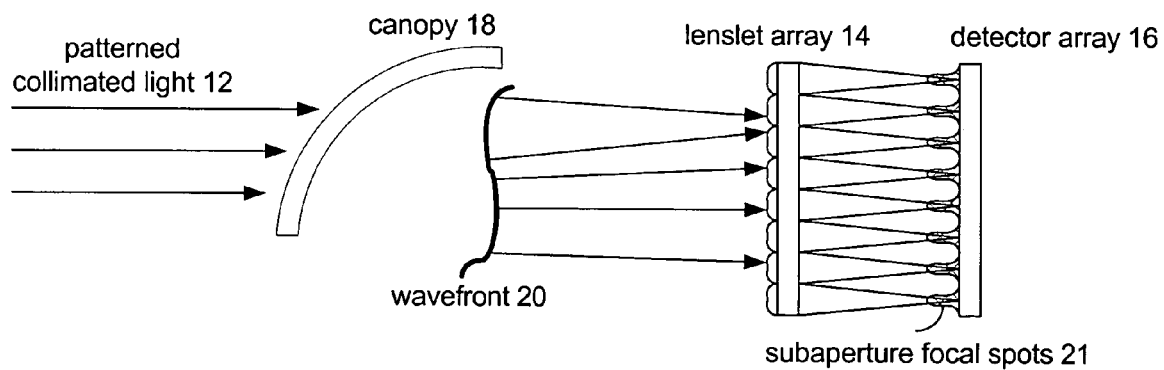
Figure 2A:
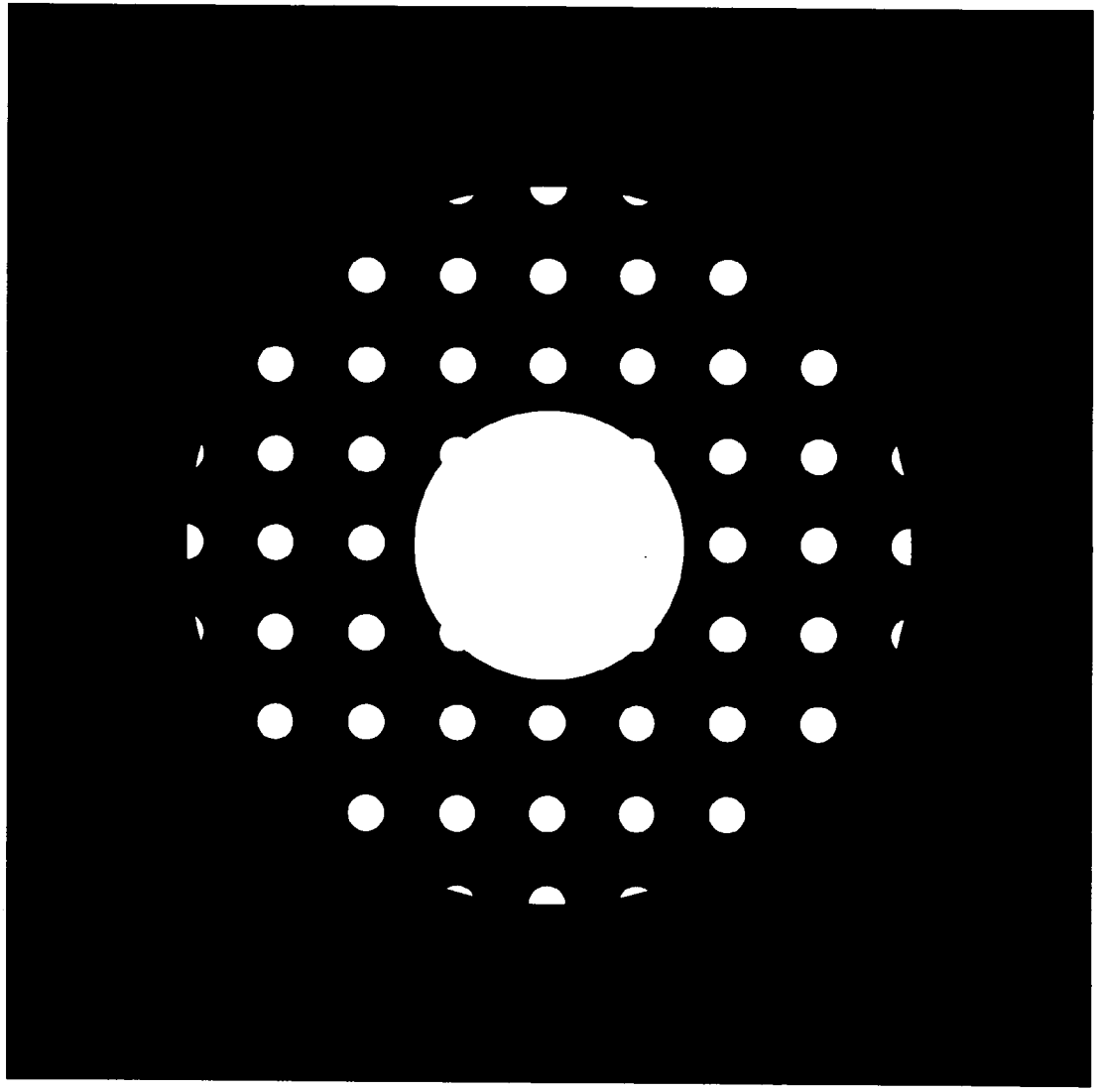
FIGS. 2A and 2B provide Hartmann spot pattern images depicting the optical deviations caused by the canopy of FIGS. 1A and 1B.
Figure 2B:
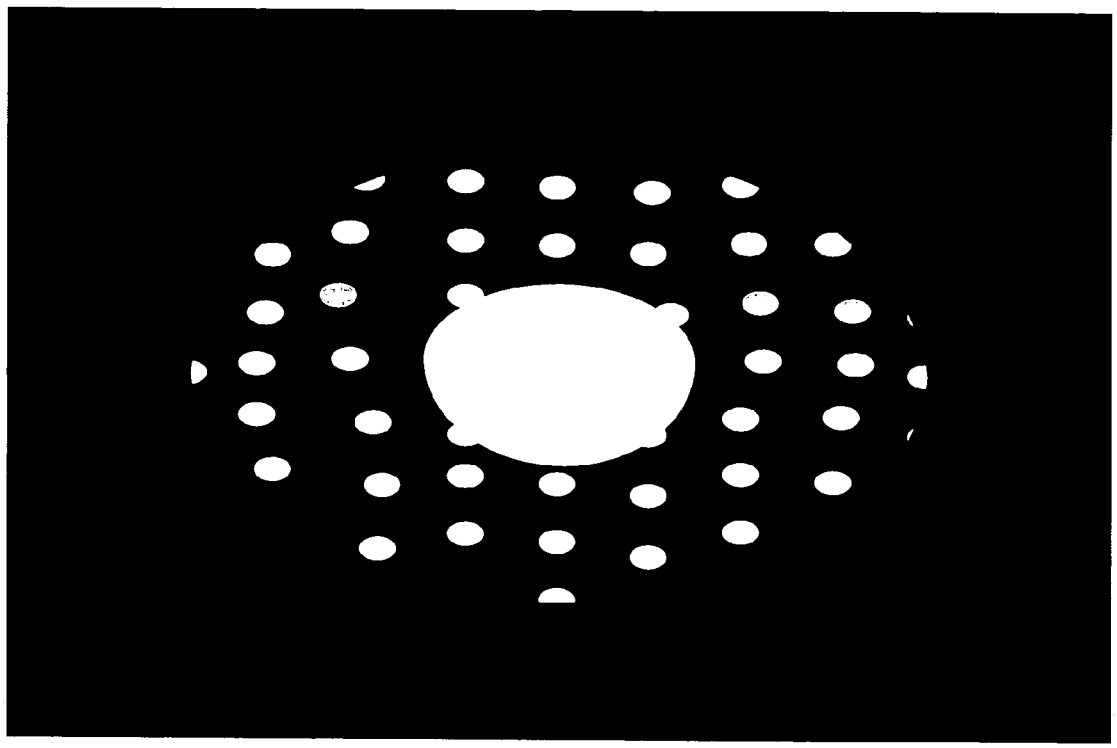

FIGS. 1A and 1B illustrate the optical effects the canopy has on an incoming wave front. The effects of the arrangements of FIGS. 1A and 1B are shown in FIGS. 2A and 2B, respectively. In FIG. 1A, a collimator supplies a collimated beam of light that is masked or patterned into subapertures to produce incoming wavefront 12. Incoming wavefront 12 is operated on by lenslet array 14. No canopy is present in FIG. 1A, thus incoming wavefront 12 is undistorted when received at lenslet array 14 and imaged using a CCD detector 16 or other like device. This undistorted image is shown in FIG. 2A.

In FIG. 1B, the collimator provides a collimated beam of light, which is patterned or masked into subapertures to produce incoming wavefront 12, which is optically distorted by canopy 18. Canopy 18 distorts wavefront 12 to produce an aberrated wavefront 20. When aberrated wavefront 20 is imaged on CCD detector 16 with lenslet array 14, a distorted image results. One can observe that the subaperture focal spots 21 are not evenly spaced on detector array 16. As shown, the subaperture focal spots 21 have shifted in two dimensions by ($\Delta$x, $\Delta$y). This is in contrast to the uniform distribution of subaperture focal spots 21 illustrated in FIG. 1A. This distorted image is illustrated in FIG. 2B.

In this example, masking or patterning the collimated light with subapertures provides an undistorted Hartmann spot set. However, other like patterns or masks known to those skilled in the art may be employed. FIG. 2B shows the same Hartmann spot pattern distorted by the optical deviations caused by the canopy. Here, spots 26 are individually shifted in the x or y position from their undistorted positions.

Figure 3:
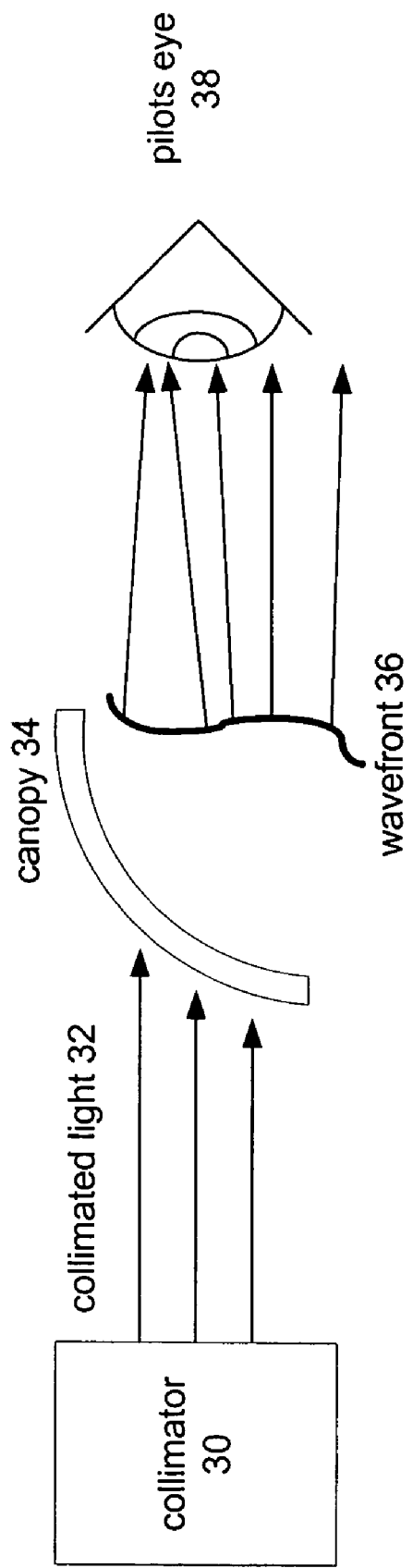
FIG. 3 provides an optical model for a tilted cylindrical canopy of FIG. 1B.

FIG. 3 provides an optical model for a tilted cylinder canopy. In this model, collimator 30 provides an optical wavefront 32, which passes through canopy 34. Optical wavefront 32 is refracted by the optical properties of canopy 34. Because canopy 34 is tilted, not all portions of wavefront 32 are acted on by the canopy at the same time. This results in further distortion of wavefront 32. The distorted wavefront 36 is imaged by pilot's eye 38 or other like imaging device located with the PEV.

Figures 4A, 4B:
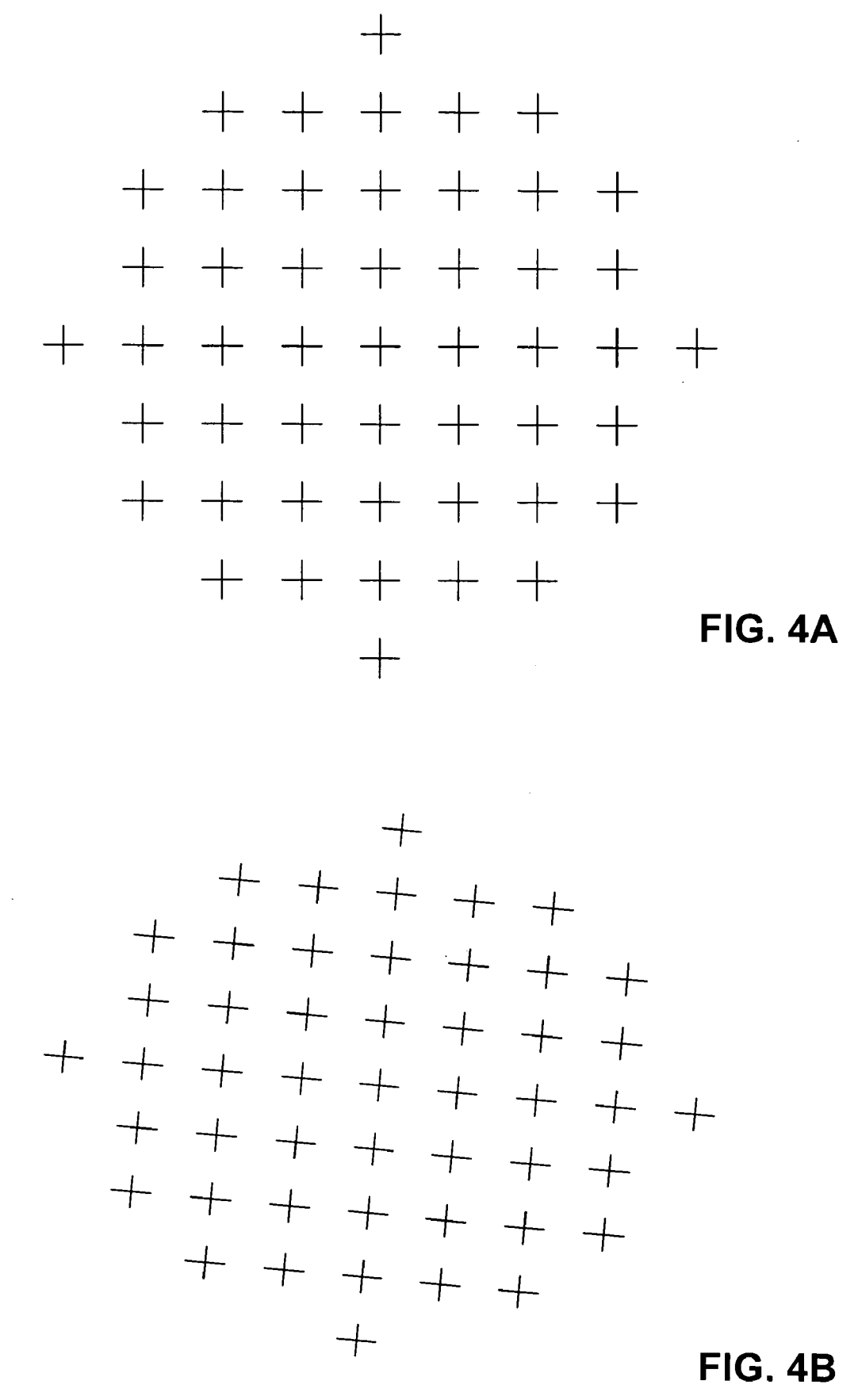
Figure 4C:
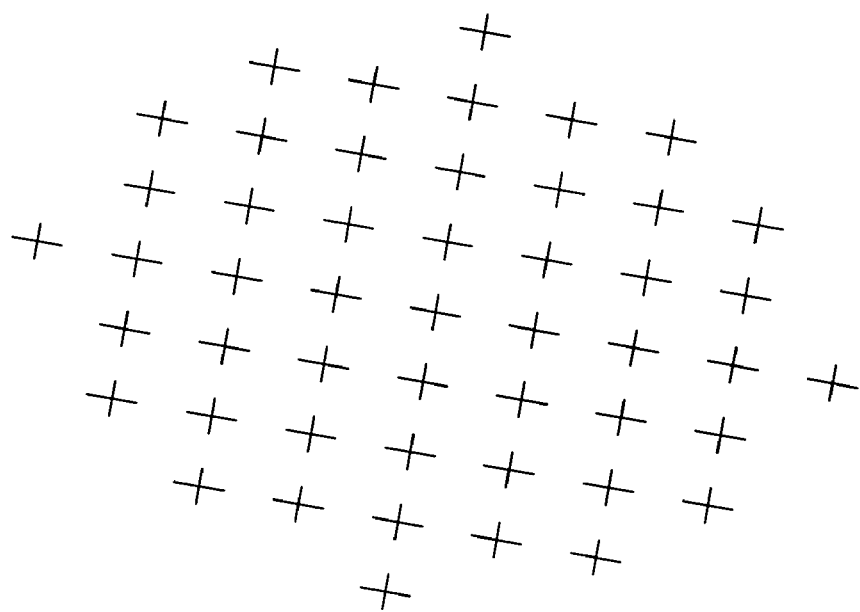
Figure 4D:
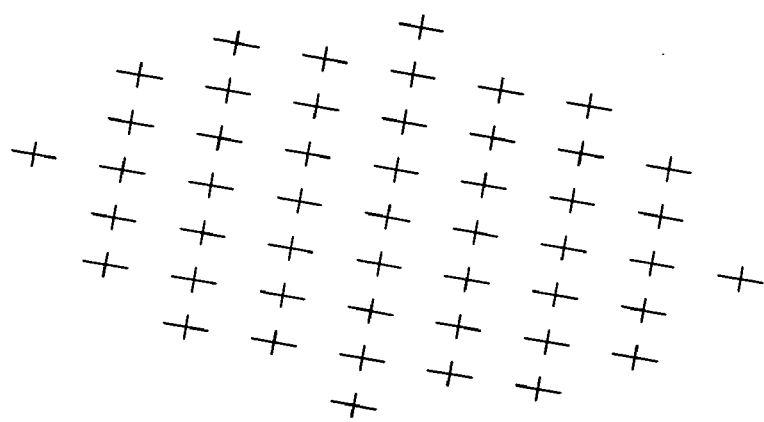
Figure 4E:
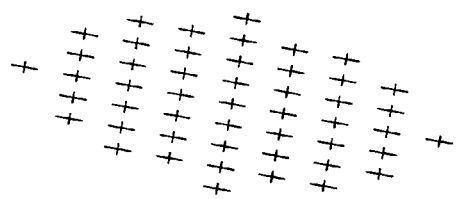

FIGS. 4A through 4E provide simulated Hartmann spots for a cylindrical canopy where the distortion of the individual points is clearly visible as one approaches closer to focus. In FIG. 4A, which is far from focus, the individual points form nearly straight lines. However, in FIG. 4E, which is much closer to focus, the distortion of the points is clearly observed.

Figure 5:
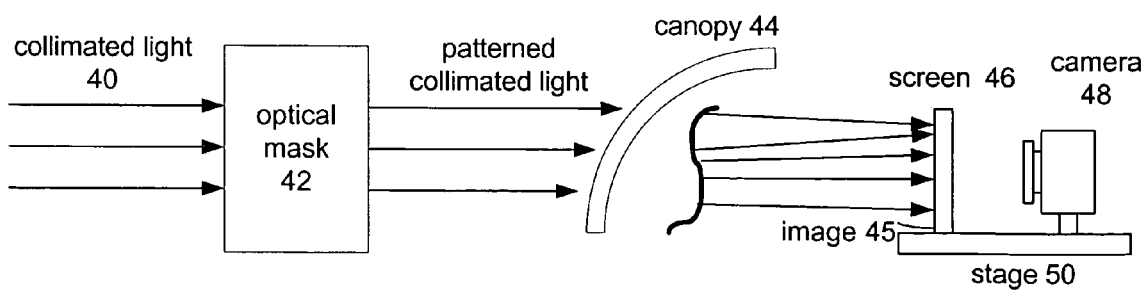
FIG. 5 depicts one configuration used to determine optical deviations associated with the canopy in accordance with the present invention.

In FIG. 5, the embodiment of the present invention depicted involves projecting a collimated light, such as a laser beam or filtered white light source, through a Hartmann mask or other like mask. This is done to pattern the collimated light which then passes through a canopy onto a ground glass screen. The screen allows an image of the patterned collimated light to be further imaged by a camera. Here, the collimated light (laser 41) passes through canopy 44 after being patterned by a Hartmann mask 42. Image 45 is captured from ground glass screen 46 with and without the optical distortions of canopy 44. Alternatively, one may compare the expected image from the Hartmann mask 42 with the image distorted by canopy 44 on ground glass screen 46. This allows one to analyze the changes in spot positions or pattern of the images. Optical deviations caused by the canopy can then be quickly and easily determined for a large area as opposed to taking a large number of individual samplings. Additionally, optical deviations may be measured for a singular angular position over a range of eye positions defined by the size of Hartmann mask 42. Camera 48 and ground glass screen 46 may be mounted on a longitudinal translation stage 50 that allows the image captured by camera 48 to be viewed from a variety of separations between camera 48 and ground glass screen 46, as well as the relative distance between ground glass screen 46 and canopy 44.

Figure 6:
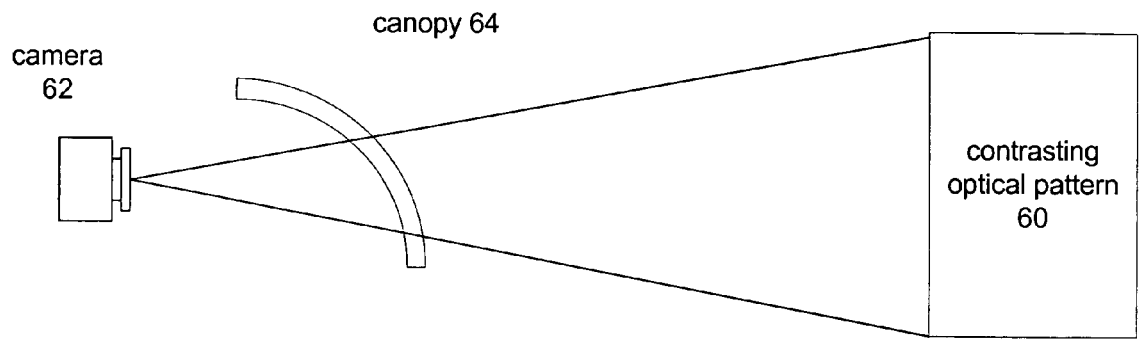
FIG. 6 provides a second embodiment used to determine optical deviations associated with the canopy in accordance with the present invention.

FIG. 6 depicts a direct image approach. Here a contrasting optical pattern, such as a large array of spots 60, is directly imaged by camera 62 located within canopy 64 at a single eye position. The optical deviations are measured by comparing the spot positions in images captured by camera 62 with and without the presence of canopy 64. This method measures a single eye position but covers a range of azimuth angles depending on the size of spot array 60. For example, one embodiment may cover +/−6° in elevation and azimuth.

Figure 7:
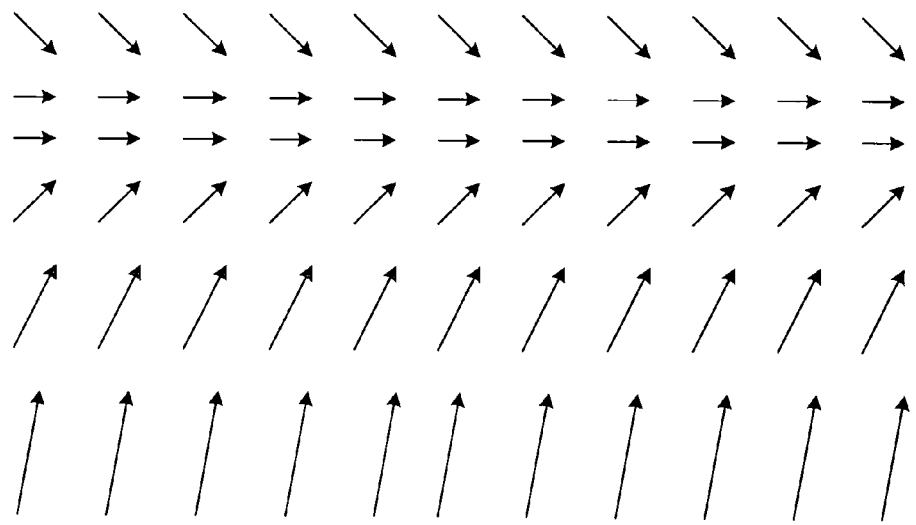
FIG. 7 is an example of direct image displacement determined in accordance with the present invention.

The target board used for spot array 60 may comprise an array of contrasting spots in a square grid. However, other contrasting patterns may be used. Additionally, this array may be located at a variety of distances from camera 62, with the canopy 64 up or down. By taking the spot images at two different target distances, as well as with and without the canopy, an interpolation algorithm generates a displacement map for each image pair. Such an apparent displacement map is shown in FIG. 7 for the farther target distance.

The displacement maps may be analyzed to resolve the wave displacement at the canopy and the angular deviation of the canopy.

Figure 8:
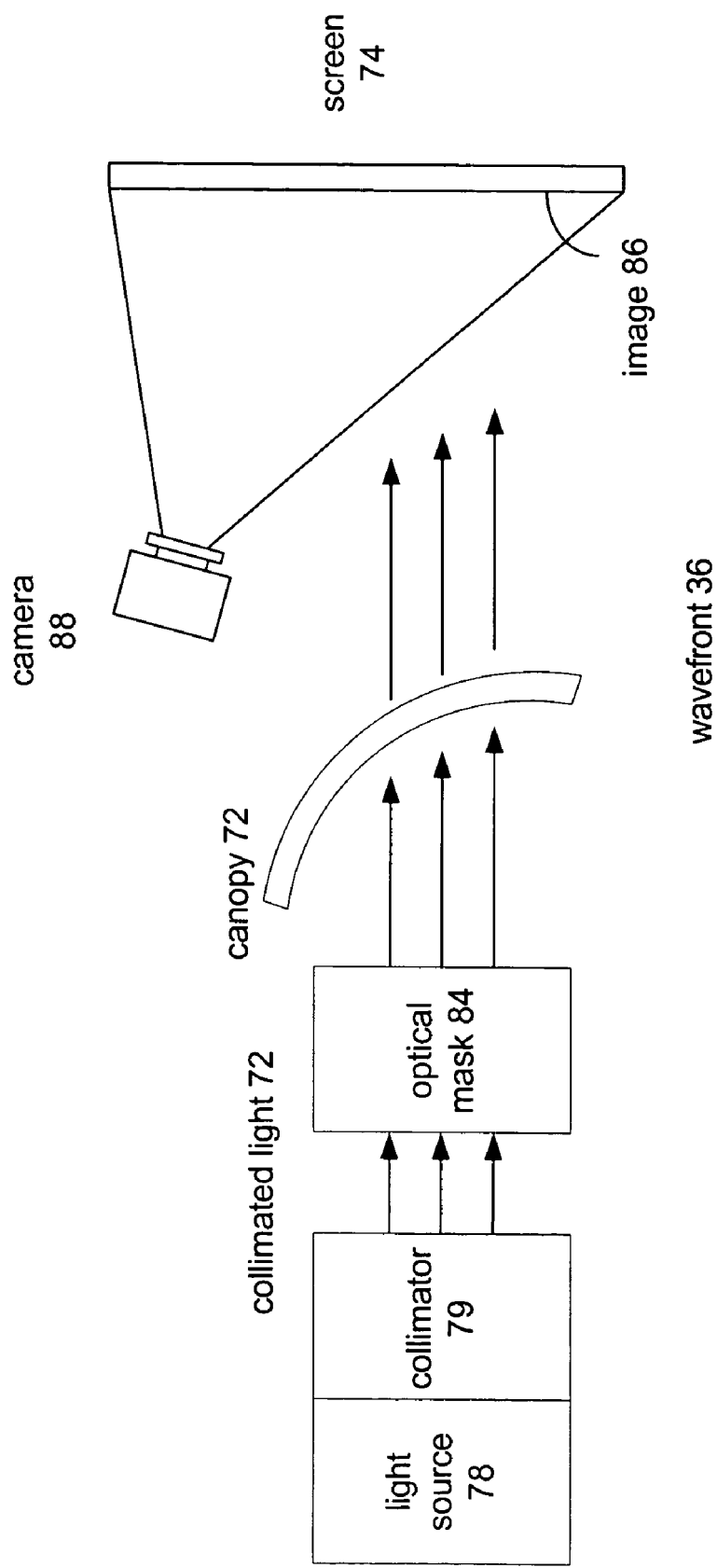
FIG. 8 depicts potential configurations set up to determine optical deviations of an aircraft canopy in accordance with embodiments of the present invention.

In FIG. 8, collimated light is projected from inside canopy 72 onto screen 74 located outside canopy 72. A pattern contained within the collimated lights 72 is imaged and recorded with screen 74. Collimated light source 78 projects collimated light 80 through a Hartmann mask 84 or other optical mask as known to those skilled in the art. The collimated light is then imaged and recorded by camera 88. The distance between screen 74 and canopy 72 may be varied to help determine the optical distortion caused by canopy 72. Images 86 are taken with the canopy up and down, allowing the angular deviations caused by the linear distance between screen 74 and canopy 72 to be determined at each position, with and without the canopy.

In another embodiment, collimated light is projected from inside the canopy onto two ground glass screens located outside the canopy. A pattern contained within the collimated light is imaged and recorded with screens. The collimated light source projects collimated light which is reflected by a pair of reflective surfaces, that pivot about a point, through a Hartmann mask or other optical mask as known to those skilled in the art. By pivoting, the light may be directed at various angles through Hartmann mask. The light passes through and is divided by beamsplitter. This allows light to be imaged on ground glass screens at different distances $d_1$ and $d_2$ from the canopy. Cameras record the images from the ground glass screens. Images, being located at different distances from the canopy are used to establish a three-dimensional vector field. Images are taken with the canopy up and down, allowing the angular deviations caused by the linear distance between screens, and canopy to be determined at each position, with and without the canopy.

A ray of light exiting canopy has direction cosines(K, L, M). These are defined as $$K = \frac{(x_2 - x_1)}{d}, L = \frac{(y_2 - y_1)}{d}, \text{ and } M = \frac{\Delta z}{d},$$

where $d=\sqrt{(x_2-x_1)^2+(y_2-y_1)^2+(\Delta z)^2}$. The elevation angular deviation "El" is the arcsine of direction cosine L, then the azimuth angular deviation is the arcsine of $$\frac{K}{\cos(El)}.$$

A processor operates on the images to define the subaperture centroids.

Figure 9A:
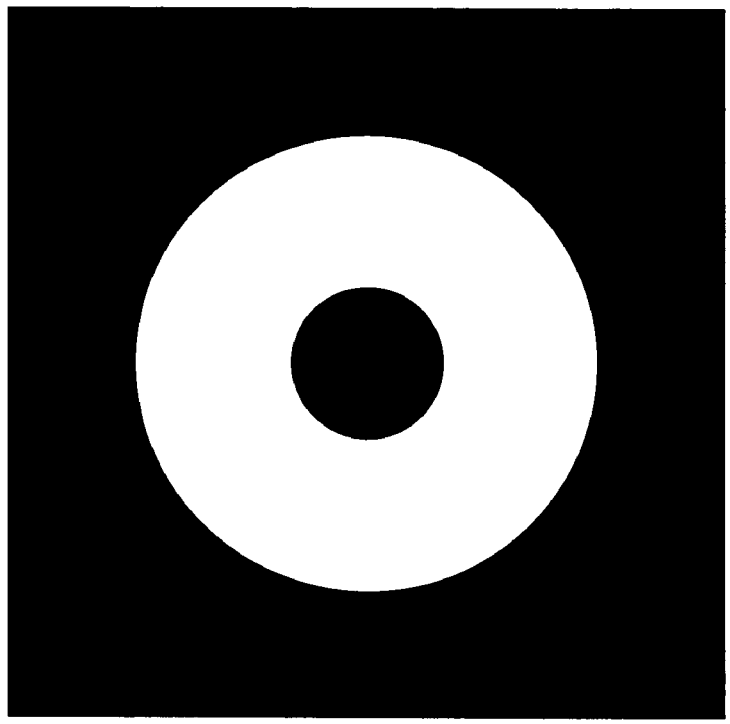
FIGS. 9A and 9B depict a perfect wave front and a warped wave front distorted by an actual aircraft canopy, respectively.
Figure 9B:
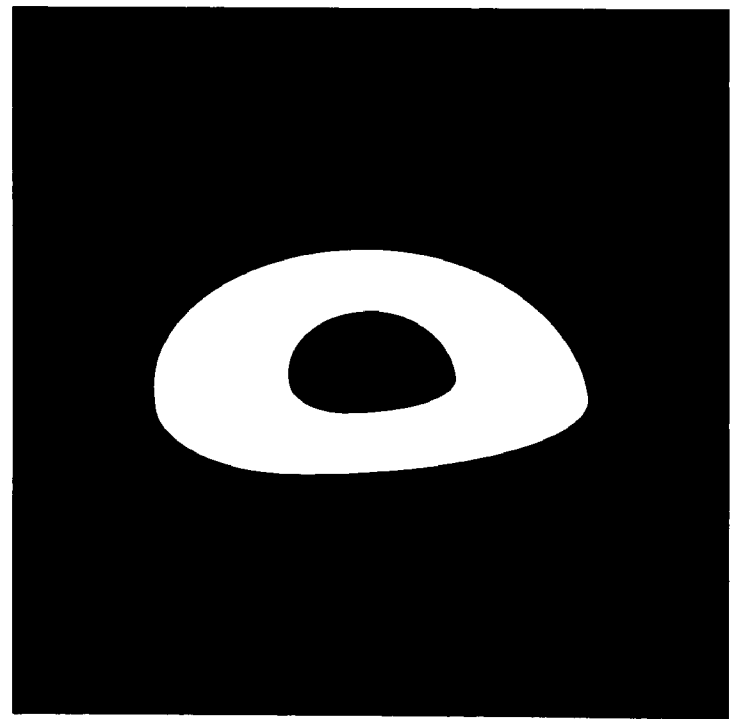

FIG. 9A depict a perfect wave front 90 with the canopy up and a zero degree elevation, which may then be compared to the distorted wavefront 92 of FIG. 9B with the canopy down. Undistorted Hartmann pattern 94 caused by the mask is shown with no distortion from the canopy in FIG. 2A and then compared to the distorted Hartmann image 96 of FIG. 2B.

Figure 10:
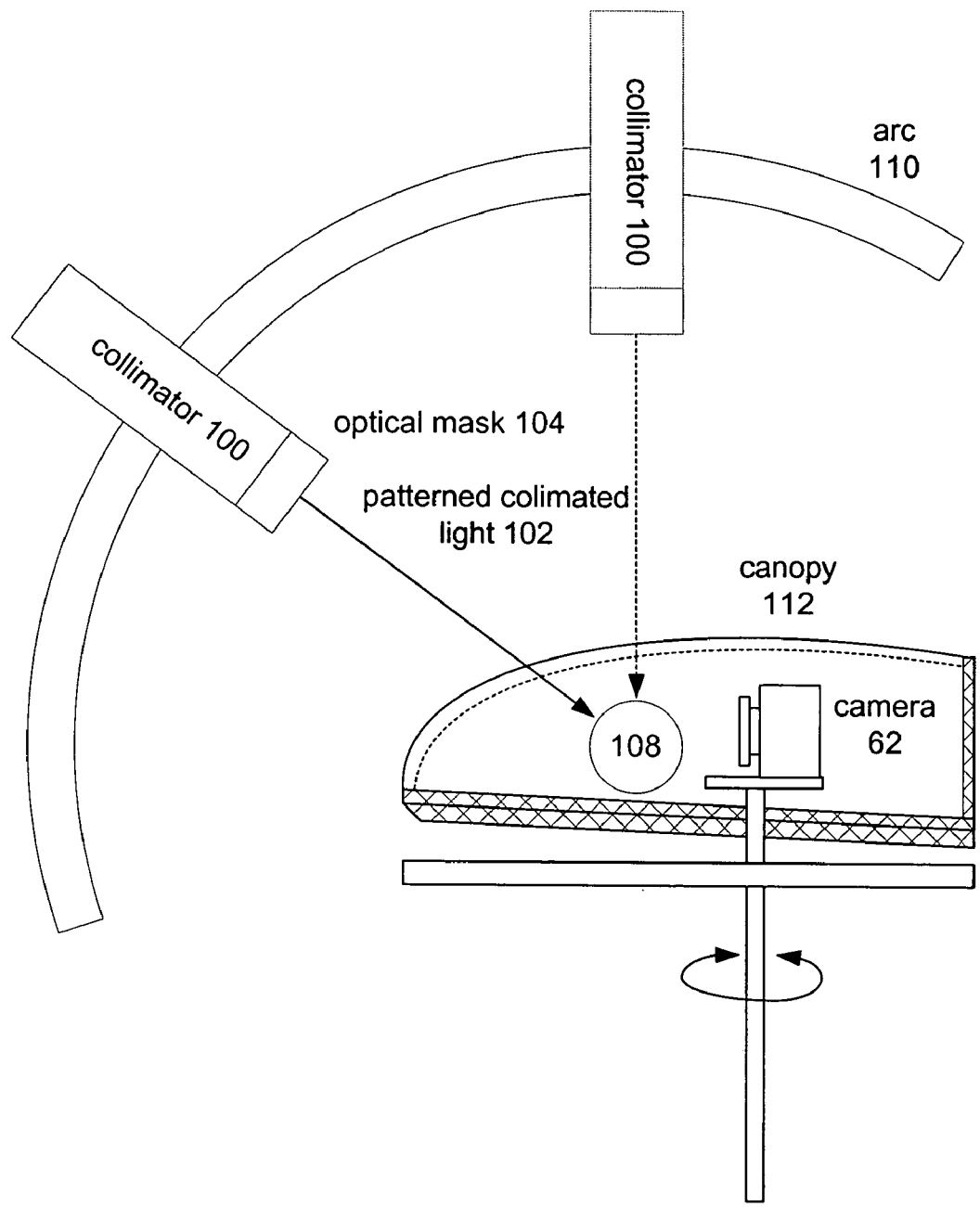
FIG. 10 provides a system to determine the optical deviations that a canopy has on incoming light received from varying elevation and azimuth angles.

FIG. 10 depicts one embodiment used to measure the optical deviations of the canopy from varying elevations and azimuth angles relative to the PEV. In this arrangement, a light source produces light to be collimated by collimator 100. Collimator 100 directs light 102 through Hartmann mask 104 or other like optical mask to produce patterned image 106 at pilot's eye centroid 108. Optical mask 104 and collimator 100 are translated in elevation angle relative to the pilot's eye centroid 108 along arc 110. Additionally, canopy 112 may be rotated in azimuth, relative to arc 110 in order to allow data to be collected on the optical distortions caused by the canopy 112 from various combinations of elevation and azimuth angles.

Figure 11:
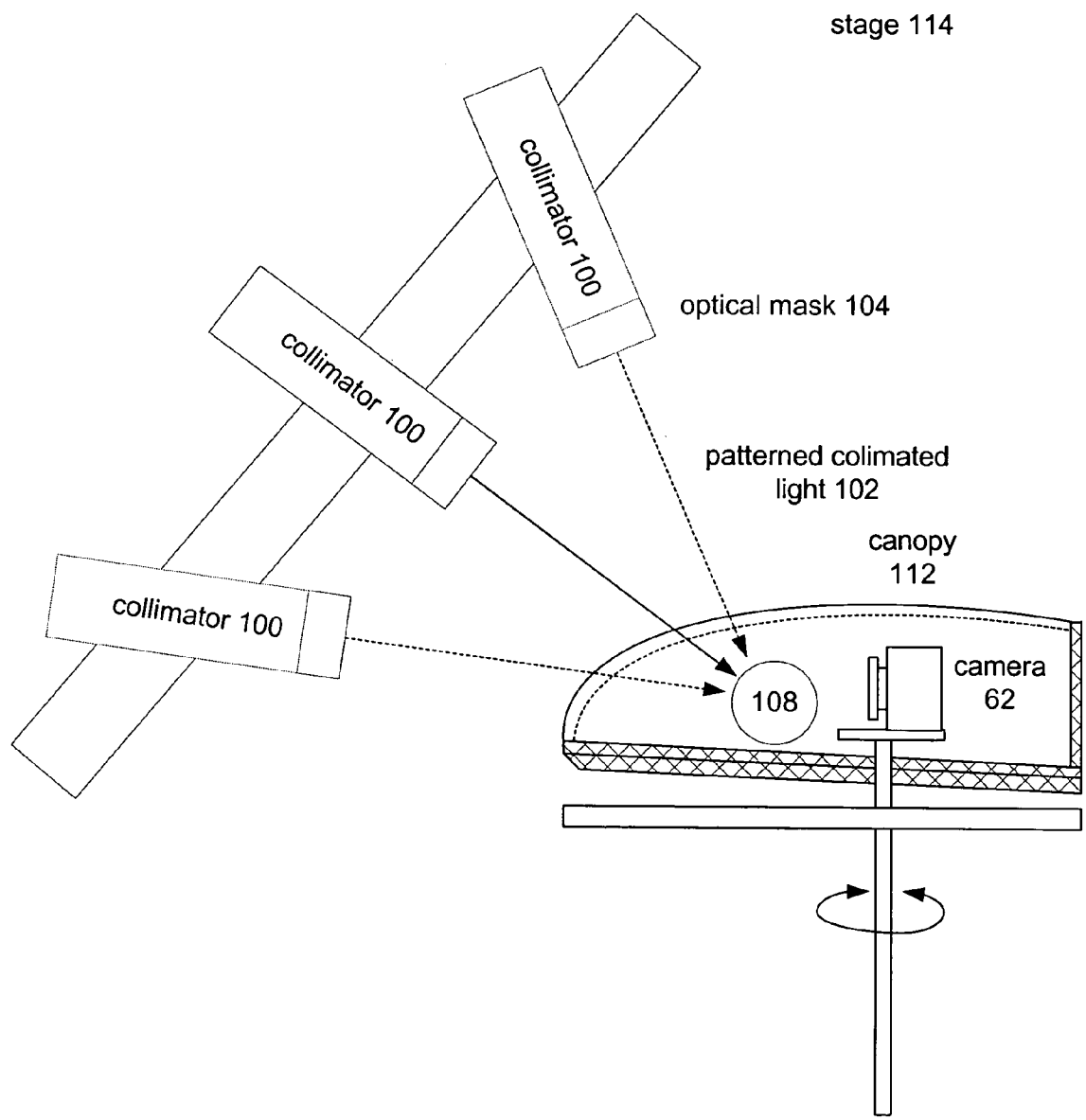
FIG. 11 provides a second embodiment of a system to determine the optical deviations of a canopy on incoming wave fronts from varying elevations and azimuth angles.

FIG. 11 depicts a second embodiment wherein collimator 100 is translated along stage 114 at varying distances and elevation angles from the pilot's eye centroid 108. Again, canopy 112 is mounted on a rotation table 116 to allow varying combinations of elevation and azimuth angle to be captured by imaging camera.

Figure 12:
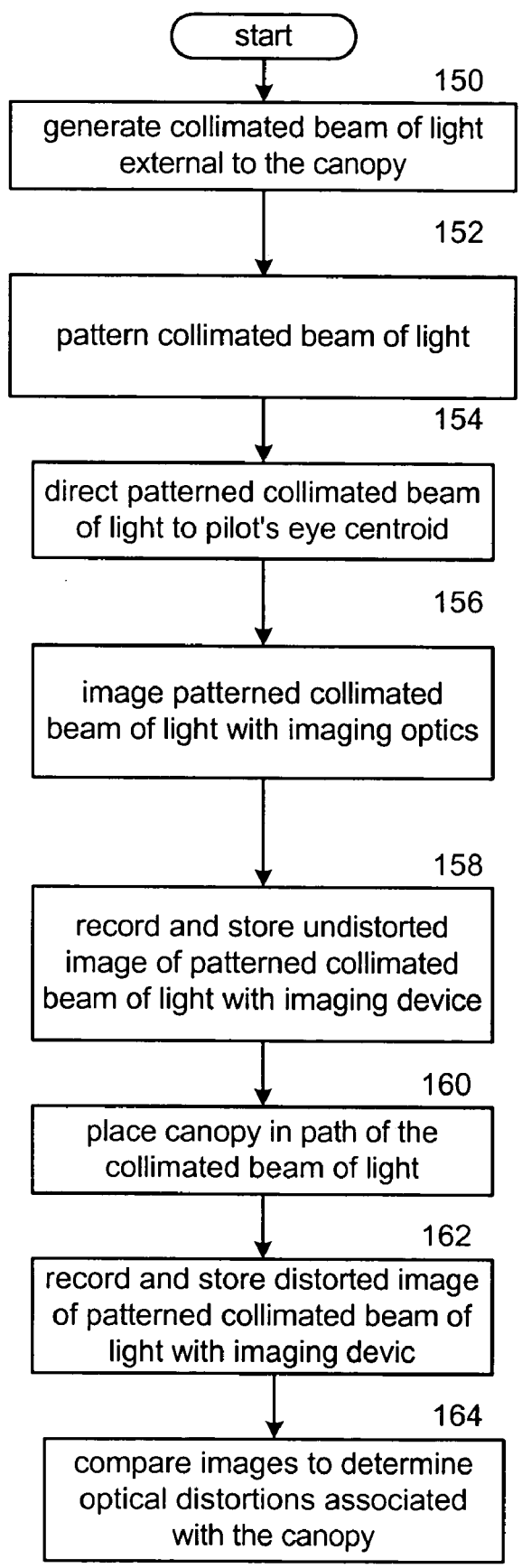
FIG. 12 is a logic flow diagram of a process to determine optical deviations of an aircraft canopy in accordance with one embodiment of the present invention.

FIG. 12 is a logic flow diagram that describes one method of determining optical deviations caused by aircraft canopy. In Step 150 a beam of collimated light is generated outside the aircraft canopy. In Step 152, the collimated beam of light passes through an optical mask to produce a patterned collimated beam of light. The patterned collimated beam of light is directed to the pilot's eye centroid within the canopy in step 154. A screen or other imaging device captures an image of the patterned collimated beam of light in step 156. At step 158, an undistorted image is captured and stored in memory. At step 160, the aircraft canopy, placed in the path of the pattern collimated beam of light, distorts the patterned collimated beam of light to produce a distorted image, which is captured and stored in memory. The distorted and undistorted images stored in memory are compared to determine the optical distortions associated with the aircraft canopy.

Figure 13:
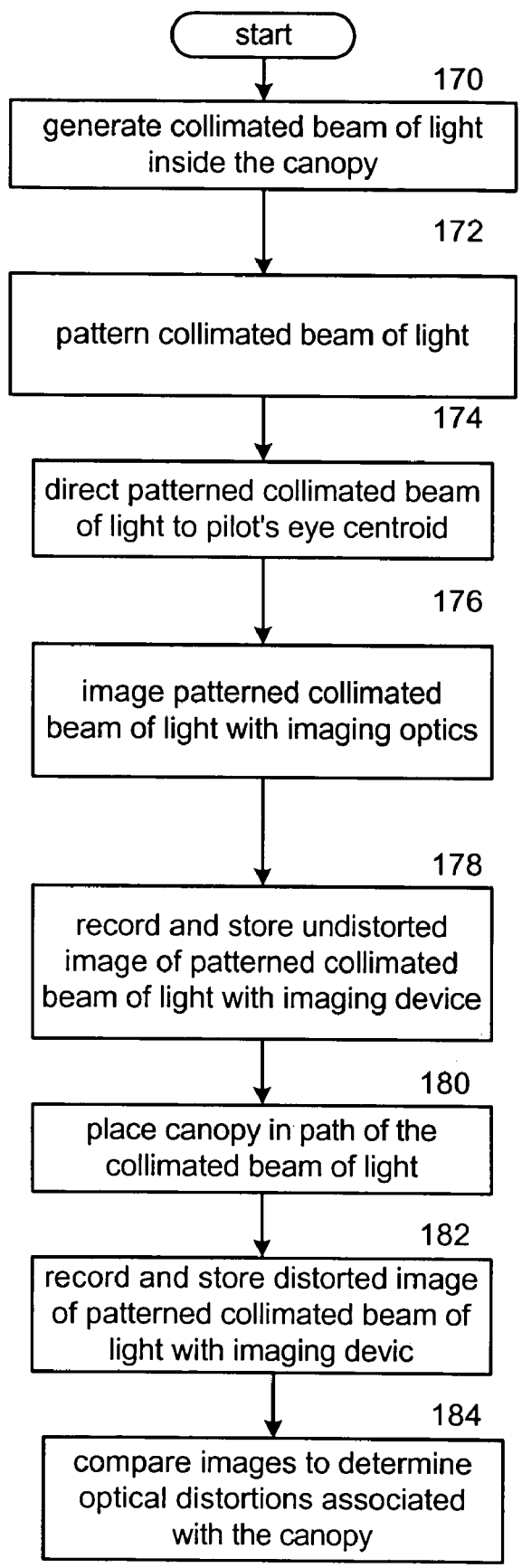
FIG. 13 is a logic flow diagram of a process to determine optical distortions of an aircraft canopy in accordance with another embodiment of the present invention.

FIG. 13 is a logic flow diagram that describes another method of determining optical deviations caused by aircraft canopy. This process is similar to that discussed in FIG. 12. However, in this instance the beam of collimated light is generated inside the aircraft canopy at step 170. In Step 172, the collimated beam of light passes through an optical mask to produce a patterned collimated beam of light. The patterned collimated beam of light is directed from the pilot's eye centroid within the canopy in step 174 to a screen or other imaging device outside the canopy. This allows the imaging device to capture an image of the patterned collimated beam of light in step 176. At step 178, an undistorted image is captured and stored in memory. At step 180, the aircraft canopy, placed in the path of the pattern collimated beam of light, distorts the patterned collimated beam of light to produce a distorted image that is captured and stored in memory. The distorted and undistorted images stored in memory are compared to determine the optical distortions associated with the aircraft canopy.

With the optical distortions known, a processor coupled to a helmet-mounted display (HMD) can dynamically generate visual queuing and symbology aligned to images received from outside the aircraft canopy. This ability greatly improves the effectiveness of the HMD and allows information to be provided to a pilot that accounts significant optical distortions of images received from outside the aircraft canopy.

Figure 14:
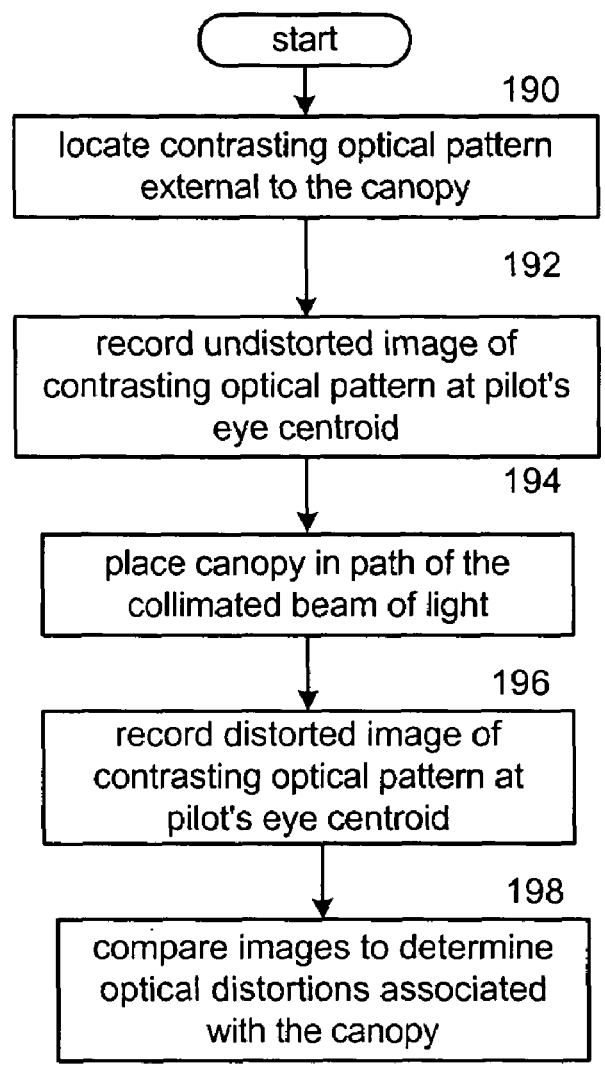
FIG. 14 is a logic flow diagram of yet another process to determine optical distortions of an aircraft canopy in accordance with yet another embodiment of the present invention.

FIG. 14 is a logic flow diagram of another embodiment that determines optical deviations caused by an aircraft canopy. In Step 190 a contrasting optical pattern is located external to the aircraft canopy. In Step 192, an undistorted image of the contrasting optical pattern is recorded with a camera located within the pilot's eye centroid. This undistorted image is stored in memory for future processing. In Step 194 the aircraft canopy is placed between the pilot's eye centroid and the contrasting optical pattern. This allows the distorted image of the contrasting optical pattern to be recorded with the camera and again stored for future processing in Step 196. These distorted images are compared to undistorted images to generate optical deviation maps associated with the aircraft canopy as well as determine other optical distortions caused by the aircraft canopy. A camera records the contrasting optical pattern, which may comprise a simple white background with a grid of contrasting spots. The size and height of the contrasting optical pattern determined the range in elevation and azimuth angles measured by the distorted and undistorted images relative to the pilot's eye centroid. Additionally, the distance between the aircraft canopy and the contrasting optical pattern may be varied between a first and second distance to produce a pair of distorted images and a pair of undistorted images. This pair of distorted and undistorted images allows an image displacement map to be made from the comparison of the distorted images to the undistorted images.

The present invention gives faster and more accurate optical deviation measurements for automobile, bus, train and truck windshields as well.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention is described in detail, it should be understood that various changes, substitutions and alterations can be made hereto without departing from the spirit and scope of the invention as described by the appended claims.

What is claimed is:

1. A method to determine optical deviations caused by an aircraft canopy that comprises:
   generating a collimated beam of light to illuminate a 3-D pilot eye volume (PEV);
   passing the collimated beam of light through an array of subapertures, each projecting a collimated beam of light;
   directing the patterned collimated beams of light to produce an undistorted image on an imaging screen, wherein the undistorted image is electronically imaged and stored in memory;
   directing the patterned collimated beam of light through the aircraft canopy, wherein the aircraft canopy distorts the patterned collimated beam of light to produce a distorted image on an imaging screen, wherein the distorted image is electronically imaged and stored in memory, and wherein a distance between the aircraft canopy and the imaging screen is varied between a first distance and a second distance;

comparing the distorted image to the undistorted image to determine the optical distortions caused by the aircraft canopy.

2. The method of claim 1, wherein the collimated beam of light is generated external to the aircraft canopy and imaging screen is located within the aircraft canopy.

3. The method of claim 1, wherein the collimated beam of light is directed to the 3-D PEV from various azimuth viewing angles and elevation viewing angles over the 3-D PB V.

4. The method of claim 1, wherein the collimated beam of light is generated within the aircraft canopy and imaging screen is located external to the aircraft canopy.

5. The method of claim 1, that further comprises:
recording a pair of distorted images at the first distance and second distance; and
recording a pair of undistorted images at the first distance and second distance.

6. The method of claim 1, wherein a width of the patterned collimated beam of light exceeds a width of the 3-D PEV within the aircraft canopy.

7. The method of claim 1, wherein the collimated beam of light is a filtered white light source.

8. The method of claim 1, wherein the array of small subapertures comprises a Hartmann mask.

9. The method of claim 1 that further comprises generating an image displacement map from the comparison of the distorted image to the undistorted image.

10. A method to determine optical deviations caused by an aircraft canopy that comprises:
placing a contrasting optical pattern external to the aircraft canopy;
recording an undistorted image of the contrasting optical pattern with a camera located within the 3-D PEV, wherein the undistorted image is stored in memory;
placing the aircraft canopy between the pilot's eye centoid and the contrasting optical pattern;
recording a distorted image of the contrasting optical pattern with the camera located within the 3-D PEV, wherein the distorted image is stored in memory, wherein a distance between the aircraft canopy and the contrasting optical pattern is varied between a first distance and a second distance; and
comparing the distorted image to the undistorted image to determine the optical distortions caused by the aircraft canopy.

11. The method of claim 10, wherein a size and height of the contrasting optical pattern determine the elevation and azimuth angles measured by the undistorted image and distorted image relative to the 3-D PEV.

12. The method of claim 10 that further comprises:
recording a pair of distorted images at the first distance and second distance, wherein pair of distorted images are stored in memory; and
recording a pair of undistorted images at the first distance and second distance, wherein the pair of undistorted images is stored in memory.

13. The method of claim 10 that further comprises generating an image displacement map from the comparison of the distorted image to the undistorted image.

14. An apparatus to determine optical deviations caused by an aircraft canopy that comprises:
a light source to generate a beam of light;
a collimator, optically coupled to the light source to collimate the beam of light;
a plurality of subapertures to pattern the collimated beam of light;
an imaging screen that receives the patterned collimated beam of light and produces and records images of the patterned collimated beam in memory, wherein:
an undistorted image is produced, recorded and stored in memory when the aircraft canopy is not placed in a path of the patterned collimated beam of light;
a distorted image is produced, recorded and stored in memory when the aircraft canopy is placed in a path of the patterned collimated beam of light and distorts the patterned collimated beam of light;
the light source to generate a beam of light, the collimator, and plurality of subapertures are located within the aircraft canopy and the imaging screen is located outside of the aircraft canopy; and
a distance between the aircraft canopy and the imaging screen is varied between a first distance and a second distance; and
a processing unit operable to compare the distorted image to the undistorted image and determine the optical distortions caused by the aircraft canopy.

15. The apparatus to determine optical deviations caused by an aircraft canopy of claim 14, wherein the light source to generate a beam of light, the collimator, and the optical patterning assembly are located external to the aircraft canopy and the imaging screen is located within the aircraft canopy.

16. The apparatus to determine optical deviations caused by an aircraft canopy of claim 15, wherein the collimated beam of light is directed to a 3-D PEV from varying elevation and azimuth angles external to the aircraft canopy.

17. The apparatus to determine optical deviations caused by an aircraft canopy of claim 14, wherein:
a pair of distorted images at the first distance and second distance are recorded and stored in memory; and
a pair of undistorted images at the first distance and second distance are recorded and stored in memory.

18. The apparatus to determine optical deviations caused by an aircraft canopy of claim 14, wherein a width of the patterned collimated beam of light exceeds a width of the 3-D PEV within the aircraft canopy.

19. The apparatus to determine optical deviations caused by an aircraft canopy of claim 14, wherein the collimated beam of light comprises a filtered white light source.

20. The apparatus to determine optical deviations caused by an aircraft canopy of claim 14, wherein the plurality of subapertures comprise a Hartmann mask.

21. The apparatus to determine optical deviations caused by an aircraft canopy of claim 14, wherein the processing unit generates an image displacement map from the comparison of the distorted image to the undistorted image.

22. An apparatus to determine optical deviations caused by an aircraft canopy that comprises:
a contrasting optical pattern external to the aircraft canopy, wherein a distance between the aircraft canopy and the contrasting optical pattern is varied between a first distance and a second distance;
a camera located within the 3-D PEV operable to record:
an undistorted image when the aircraft canopy is not placed in a path of the patterned collimated beam of light;
a distorted image when the aircraft canopy is placed in the path of the patterned collimated beam of light and distorts the patterned collimated beam of light;

a processing unit operable to:
receive and store the undistorted image and distorted image in memory coupled to the processing unit;
compare the distorted image to the undistorted image and determine the optical distortions caused by the aircraft canopy.

23. The apparatus to determine optical deviations caused by an aircraft canopy of claim 22, wherein a size and height of the contrasting optical pattern determine the elevation and azimuth angles measured by the undistorted image and distorted image relative to the 3-DPEV.

24. The apparatus to determine optical deviations caused by an aircraft canopy of claim 22, wherein the camera is further operable to:

record a pair of distorted images at the first distance and second distance, wherein pair of distorted images are stored in memory; and record a pair of undistorted images at the first distance and second distance, wherein pair of undistorted images are stored in memory.

25. The apparatus to determine optical deviations caused by an aircraft canopy of claim 24, wherein the processing unit is further operable to generate an image displacement map from the comparison of the distorted image to the undistorted image.

* * * * *